United States Patent
Chien et al.

(10) Patent No.: US 12,009,785 B2
(45) Date of Patent: Jun. 11, 2024

(54) HIGH-THROUGHPUT MULTIPLEXED RECORDING

(71) Applicant: The Board of Trustees of the Leland Stanford Junior University, Stanford, CA (US)

(72) Inventors: Jun-Chau Chien, Palo Alto, CA (US); Mohammad Amin Arbabian, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 385 days.

(21) Appl. No.: 17/413,518

(22) PCT Filed: Dec. 13, 2019

(86) PCT No.: PCT/US2019/066373
§ 371 (c)(1),
(2) Date: Jun. 11, 2021

(87) PCT Pub. No.: WO2020/124030
PCT Pub. Date: Jun. 18, 2020

(65) Prior Publication Data
US 2022/0052641 A1    Feb. 17, 2022

Related U.S. Application Data

(60) Provisional application No. 62/779,420, filed on Dec. 13, 2018.

(51) Int. Cl.
*H03B 5/02* (2006.01)
*H03B 5/12* (2006.01)
(Continued)

(52) U.S. Cl.
CPC ............. *H03B 5/02* (2013.01); *H03B 5/1203* (2013.01); *H04L 5/06* (2013.01); *A61N 1/0529* (2013.01)

(58) Field of Classification Search
CPC ........... H03B 5/02; H03B 5/1203; H04L 5/06; A61N 1/0529
See application file for complete search history.

(56) References Cited

U.S. PATENT DOCUMENTS 3,510,565 A   5/1970   Morez
4,211,893 A   7/1980   Smith
(Continued)

OTHER PUBLICATIONS

Jeutter, D.C. et al. (Sep. 1, 1993). "Design of a Radio-Linked Implantable Cochlear Prosthesis Using Surface Acoustic Wave Devices," IEEE Transactions on Ultrasonics, Ferroelectrics, and Frequency Control 40(5):469-477.
(Continued)

*Primary Examiner* — Henry Tsai
*Assistant Examiner* — Christopher A Daley
(74) *Attorney, Agent, or Firm* — Mintz Levin Cohn Ferris Glovsky and Popeo, P.C.

(57) ABSTRACT

In some embodiments, there is provided an apparatus including a common bus and a plurality of oscillatrode circuits coupled to the common bus, the plurality of oscillatrode circuits including a first oscillatrode circuit outputting a first frequency tone when a first input voltage is detected by the first oscillatrode circuit and a second oscillatrode circuit outputting a second frequency tone when a second input voltage is detected by the second oscillatrode circuit, wherein common bus carries the first frequency tone and the second frequency tone at different frequencies in a frequency division multiplex signal. Related systems, methods, and articles of manufacture are also disclosed.

18 Claims, 16 Drawing Sheets

(51) Int. Cl.
  *H04L 5/06* (2006.01)
  *A61N 1/05* (2006.01)

(56) References Cited

U.S. PATENT DOCUMENTS

| | | | |
|---|---|---|---|
| 5,037,376 | A | 8/1991 | Richmond et al. |
| 5,608,724 | A | 3/1997 | Green, Jr. |
| 8,914,118 | B2 * | 12/2014 | Hasulak ............... A61N 1/0534 |
| | | | 607/45 |
| 9,967,039 | B2 * | 5/2018 | Kim ...................... H04L 5/0048 |
| 10,857,348 | B2 * | 12/2020 | Greger .................. A61B 5/685 |
| 2009/0118804 | A1 * | 5/2009 | Moffitt ................. A61B 5/6864 |
| | | | 607/116 |
| 2010/0106041 | A1 * | 4/2010 | Ghovanloo .......... A61B 5/0006 |
| | | | 607/116 |
| 2017/0007824 | A1 * | 1/2017 | Gardner ............... A61N 1/0529 |
| 2020/0289061 | A1 * | 9/2020 | Rapoport ............. A61L 31/022 |
| 2021/0407678 | A1 * | 12/2021 | Arcot Desai ............. G06F 8/65 |

OTHER PUBLICATIONS

Julian Warchall, A. et al. (May 22, 2016). "A Multi-Channel EEG System Featuring Single-Wire Data Aggregation via FM-FDM Techniques," 2016 IEEE International Symposium on Circuits and Systems (ISCAS), pp. 526-529.

Rajabi-Tavakkol, A. et al. (Aug. 31, 2010). "New Architecture for Wireless Implantable Neural Recording Microsystems Based on Frequency-Division Multiplexing," $32^{nd}$ Annual International Conference of the IEEE EMBS, Buenos Aires, Argentina, Aug. 31-Sep. 4, 2010, pp. 6449-6452.

\* cited by examiner

900

Receiving, at a first array of electrodes, a first plurality of signals sensed from neural tissue inside a cranium 905

Modulating each of the first plurality of signals to form a first output signal 910

Coupling the first output signal to a first bus to enable the first bus to carry the first output signal through a cranium 920

FIG. 9

HIGH-THROUGHPUT MULTIPLEXED RECORDING

CROSS REFERENCE TO RELATED APPLICATION

This application is a national phase entry of Patent Cooperation Treaty Application No. PCT/US2019/066373 filed Dec. 13, 2019, entitled "HIGH-THROUGHPUT MULTIPLEXED RECORDING," which claims priority to U.S. Provisional Patent Application No. 62/779,420 filed on Dec. 13, 2018, entitled "HIGH-THROUGHPUT SIMULTANEOUS RECORDING AT MASSIVE SCALE," the disclosures of which are incorporated herein by reference in their entirety.

BACKGROUND

Neural probes may be used to perform measurements on brain tissues. State-of-the-art electrophysiological neural recording using neural probes may suffer from a trade-off between spatial, temporal, and sensitivity resolution. As such, neural probes may be limited in the amount of sensor data that can be carried back to other devices for testing, measuring, and/or monitoring.

SUMMARY

In some embodiments, there is provided an apparatus including a common bus and a plurality of oscillatrode circuits coupled to the common bus, the plurality of oscillatrode circuits including a first oscillatrode circuit outputting a first frequency tone when a first input voltage is detected by the first oscillatrode circuit and a second oscillatrode circuit outputting a second frequency tone when a second input voltage is detected by the second oscillatrode circuit, wherein common bus carries the first frequency tone and the second frequency tone at different frequencies in a frequency division multiplex signal.

In some variations, one or more of the features disclosed herein including the following features can optionally be included in any feasible combination. The first oscillatrode circuit may include an electrode coupled to a transistor, the transistor further coupled to an oscillator, wherein when the first input voltage is detected, the electrode carries the first input voltage to activate the transistor, the transistor outputting a voltage that initiates the oscillator to output the first frequency tone. The oscillator may include a ring oscillator. The transistor may include a field effect transistor. The first electrode may include a neural penetrating probe. The first input voltage may be a neural voltage generated by neural cells. The common bus and the plurality of oscillatrode circuits may be implanted within a cranial cavity. The common bus may provide, via a wired link or a wireless link, the frequency division multiplex signal to a receiver external to the cranial cavity. The apparatus may include, or be included in, a neural probe configured to be implanted within the cranial cavity. The receiver may demodulate the frequency division multiplex signal to detect signals representative of the first input voltage and/or the second input voltage.

In some embodiments, there is provided a method. The method may include receiving, at a first array of electrodes, a first plurality of signals sensed from neural tissue inside a cranium; modulating each of the first plurality of signals to form a first output signal; and coupling the first output signal to a first bus to enable the first bus to carry the first output signal through a cranium.

In some variations, one or more of the features disclosed herein including the following features can optionally be included in any feasible combination. Each of the first plurality of signals may be modulated in frequency to form the first output signal comprising a frequency division multiplexed signal. The first plurality of signals may be modulated in frequency by a plurality of oscillators coupled to the first plurality of electrodes. Each of the first plurality of signals may be modulated in phase to form the first output signal comprising a phase modulated signal. The bus may wirelessly carry the first output signal through the cranium via a wireless link. The bus may carry the first output signal through the cranium via a wired link. The method may be performed on a neural probe. The neural probe may be inserted on neural tissue within a cavity defined by the cranium. The method may further include receiving, at a demodulator, the first output signal traversing the cranium, and demodulating the received first output signal to detect signals representative of the first plurality of signals sensed by the first array of electrodes. The method may include receiving, at a second array of electrodes, a second plurality of signals sensed from neural tissue inside the cranium, modulating each of the second plurality of signals to form a second output signal, and coupling the second output signal to a second bus to enable the second bus to carry the second output signal through the cranium towards the demodulator.

Implementations of the current subject matter can include systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 9 depicts an example process 900, in accordance with some example embodiments.

DETAILED DESCRIPTION

Neural probes may, as noted, be used to perform measurements on brain tissues. State-of-the-art electrophysiological neural recording using neural probes may suffer from a trade-off between spatial, temporal, and sensitivity resolution. As such, neural probes may be limited in the amount of sensor data that can be carried back to other devices, such as testing and/or monitoring equipment.

The subject matter disclosed herein presents a massive recording technique to overcome the physical limitation induced by the interconnections for electrophysiological recording in multiple regions of brain cortex. To reach the goal of simultaneous recording at the massive scale, the subject matter disclosed herein provides a multiplexing technique that transduces the voltage signals from different recording pixels (e.g., probes, electrodes, contacts, and/or the like) to a group of frequency carriers, which can be transmitted through a single wire, such as a bus, to a receiver, such as a sensor hub for demodulation. This approach may enable significant increase in recording density by simplifying the hardware placed underneath the recording electrodes while shifting the power-hungry and area-demanding signal processing circuitries to the appropriate location outside the cranium where resources are of less constraint. Moreover, the subject matter disclosed herein may provide a wireless-first concept to further shift some of the necessary signal processing to the outside of the cranium. The subject matter disclosed herein may also enable the distribution of multiple neural recording probes and the Electrocorticography (ECoG) surface electrodes within different parts of the brain cortex, enabling the study of correlation between the complex neural network and the external environment and stimulus.

Although some of the examples described herein refer to a neural application, the disclosed system and methods may be applicable to other large-scale, array-based sensing and/or measurement applications where throughput, temporal resolution, and/or simultaneously parallel recording are desired or necessary.

In some example embodiments, there is provided a neural probe providing high-density measurements using frequency-division multiplexing (FDM). The neural probe includes so-called "oscillatrode" circuits having an array of oscillators, such as ring oscillators, embedded as part of the neural probe's electrodes. Each of the plurality of oscillatrode circuitry (which form an array) may directly modulate a neural signal onto a single wire, such as a bus, without additional processing such as analog-to-digital conversion. Moreover, the oscillatrode circuitry array may operate at carrier frequencies that are not strictly pre-defined but instead randomness and/or other techniques may be used to create the frequency channels (and corresponding frequency spacing) for each oscillatrode circuit.

Figure 1A:
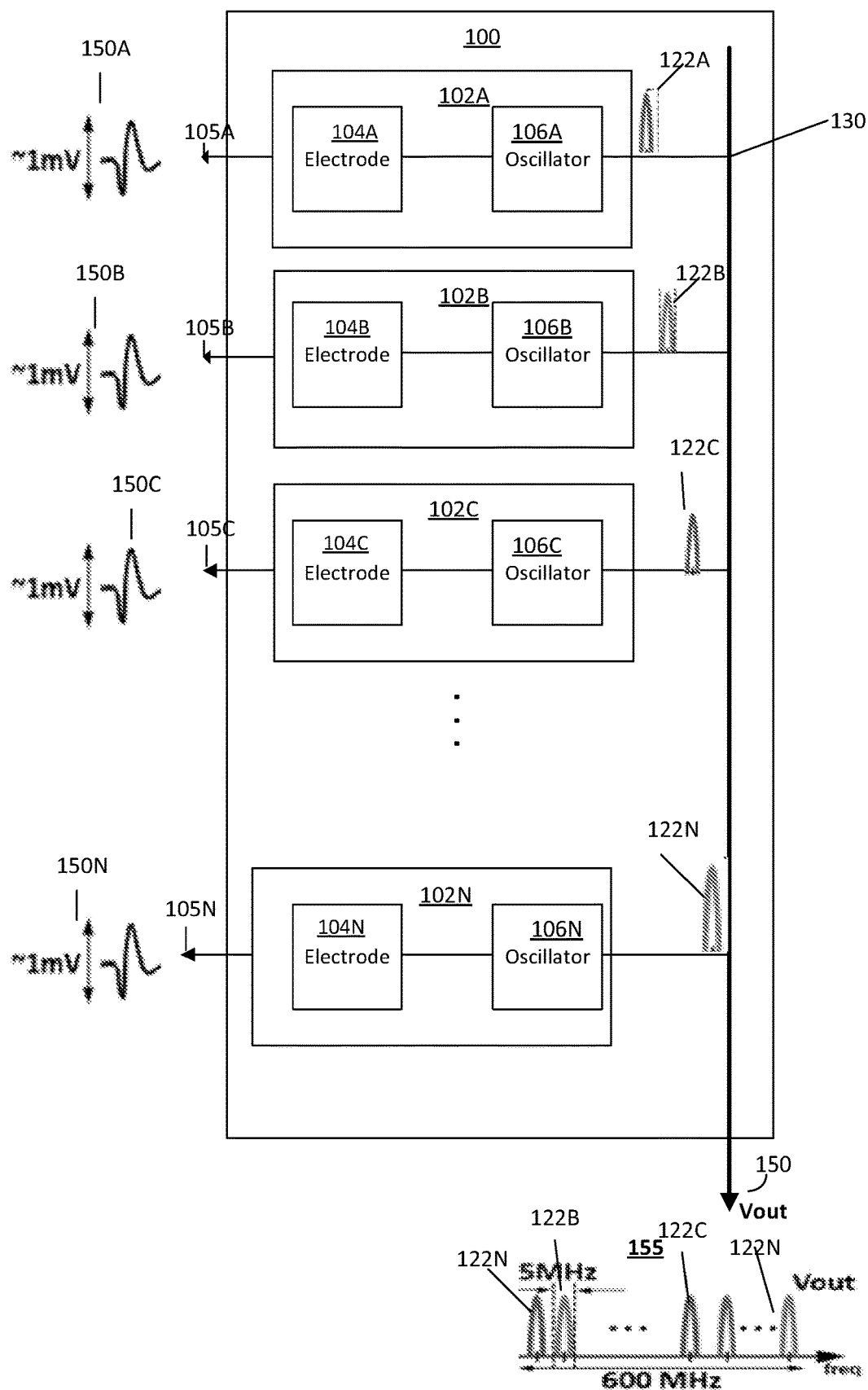
FIGS. 1A-1B depict examples of systems for frequency division multiplexing sensed signals, in accordance with some example embodiments.

FIG. 1A depicts an example of a system 100, in accordance with some example embodiments. In the example of FIG. 1A, the system may include a plurality of electrode-oscillator circuits 102A-N. The electrode-oscillator circuit may also be referred to herein as an oscillatrode circuit. This novel circuit 102A may include an oscillator 106A and may include, or be coupled to, an electrode 104A (hence the name oscillatrode). The electrode may make contact with a portion of neural tissue being sensed, such as tested, monitored, measured, and/or the like. Alternatively, or additionally, the electrode may comprise a penetrating probe, in which case the electrode 104A may include a penetrating probe 105A portion to make contact and/or penetrate a portion of the neural tissue.

The oscillator circuit 106A may comprise a ring oscillator circuit. In the example of FIG. 1A, the oscillator circuit may be configured to provide (or vary) the oscillator circuit's output frequency as a function of oscillator circuit's input voltage. For example, if neural tissue is activated, it may cause a neural signal 150A having a certain voltage (which in the example of FIG. 1A is about 1 millivolt, although other voltages may be realized as well). The neural signal 150 is received by the penetrating probe 105A including electrode circuitry 104A, which is then received as an input at the oscillator circuit 106A. The oscillator circuit may then generate an output signal 122A at a first frequency when the input, neural signal is present or detected. This output signal 122A is then coupled to a bus 130. The bus 130 may, preferably, implemented as a single wire. The wire may consist of a conductive material, such as aluminum, copper, titanium, material compliant with fabrication technology such as CMOS VLSI fabrication, and/or other conductive material compatible with (e.g., not harmful to and/or reactive with) tissue such as the neural tissue being probed.

The system 100 may, as noted, include a plurality of oscillatrode circuits 102A-N. For example, the oscillatrode circuit 102B may also include an oscillator circuit 106B, such as a ring oscillator circuit. In the example of FIG. 1A, when neural tissue is activated, it may cause a neural signal 150B having a certain voltage to be detected and/or received by the penetrating probe 105B including electrode circuitry 104B. This neural signal 150B may be received as an input at the oscillator circuit 106B, which generates output signal 122B at a second frequency when the input, neural signal is present and detected. This output signal 122B is also coupled to a bus 130.

As such, each of the oscillatrode circuits 102A-N may generate a corresponding output signal at a given frequency, when there are neural signals 150A-N active. For example, oscillatrode circuit 102A may generate a frequency tone output 122A, when neural signal 150A is present and detected. These corresponding output signals (or frequency tones which generated by the oscillatrode circuits 102A-N) may form a frequency division multiplex (FDM) signal carried by a common bus 130. An example of the FDM signal 155 is shown at FIG. 1A. In other words, each of the oscillatrode circuits 102A-N may be configured to generate a frequency tone (when there is a corresponding neural signal 102A-N), and the frequency tones may be separate, non-overlapping frequencies carried by the single wire bus 130. The frequency multiplexed tones may thus advantageously enable the neural probe to include a large array of oscillatrode circuits.

Although the previous example describes a single wire bus, a plurality of wires may be used as well. For example, a first set of oscillatrodes may be coupled to a first wire serving as a common bus, while a second set of oscillatrodes may be coupled to a second wire serving as a common bus for the second set.

In some example embodiments, the system 100 is mounted within a cranium to allow the electrodes 104A-N and penetrating probes 105A-N to make contact with the neural tissue under test. When this is the case, the FDM signal 155 (generated by the oscillatrode circuits 102A-N) is carried by the common bus 130 and output at Vout 150 through the cranium to a receiver for demodulating the FDM signal for further processing of the neural measurements. In some example embodiments, Vout 150 is carried via a wired link through the cranium to the receiver. In some example embodiments, Vout 150 is carried via a wireless link through the cranium to the receiver.

Figure 1B:
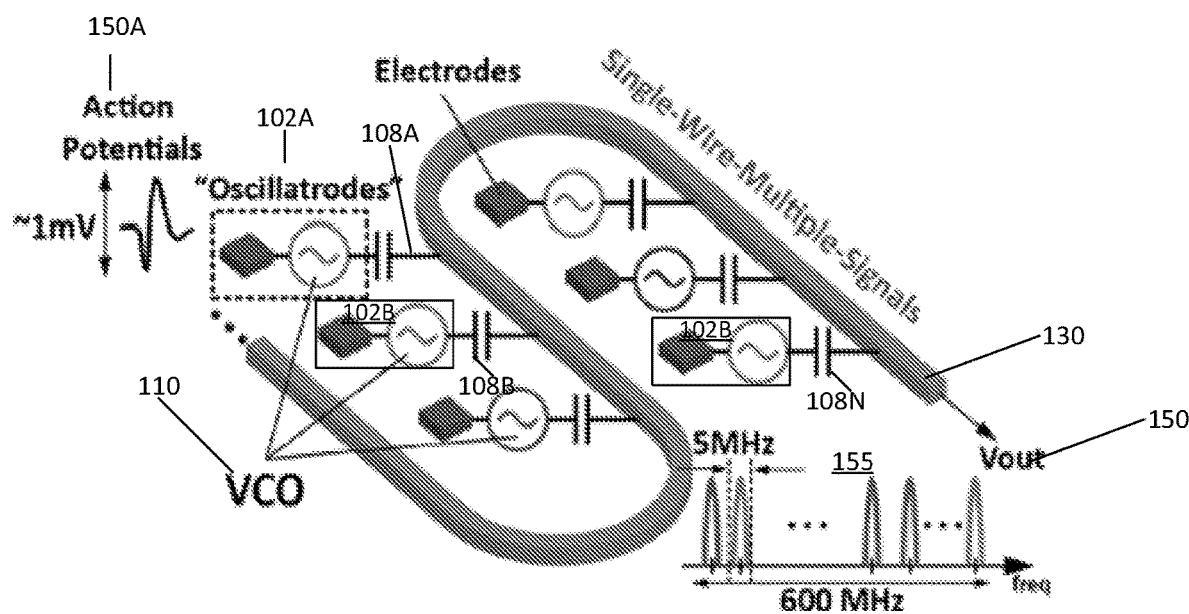

FIG. 1B depicts another example of system 100, in accordance with some example embodiments. FIG. 1B is similar to FIG. 1A in some respects but also depicts a coupling element, such as capacitor 108A, to couple the output of the oscillatrode circuits 102A to the bus 130. Each of the oscillatrode circuits may have a corresponding coupling capacitor 102B-N (as shown) to couple to the bus 130.

In some example embodiments, the system 100 may be suitable for scaling toward massive-scale neural recording (more than 1,000,000 pixels, such as electrodes, probes, and the like) for three-dimensional mapping of the cortex, for example. The system 100 may implement frequency multiplexing to achieve simultaneous recording from some (if not all) probes recording neural measurements, while performing data transfer using a minimum number of wires, such as a single bus wire 130. Because of the orthogonality of FDM, signals detected by the electrodes 104A-N may be recovered with minimal crosstalk. For example, 5,000 neural probes may provide 5000 recording channels carried by a single wire bus 130 (e.g., given a 20-kHz neural spike signal creating a modulation bandwidth of 1 MHz across a frequency span of 1000 MHz), thus breaking a constraint due to wiring. Scaling toward one million recording may be achieved with a multi-wire bus at 130 (each wiring carrying a FDM signal from a set of oscillatrode circuits) for a given cranial implant and/or with the distribution of multiple implants within the cranium.

Figure 2A:
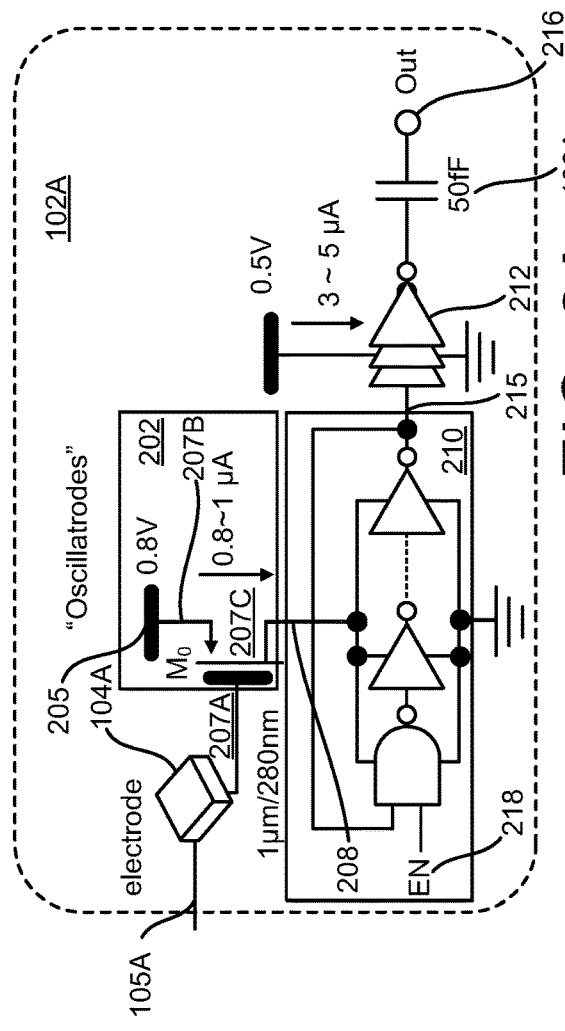
FIG. 2A depicts an example implementation of an oscillatrode circuit, in accordance with some example embodiments.

FIG. 2A depicts an example implementation of the oscillatrode circuit 102A, in accordance with some example embodiments. The oscillatrode circuit may include an input stage comprising the electrode 104A and/or the penetrating probe 105A. The electrode 104A and/or penetrating probe 105A may be made of a conductive material, such as titanium, iridium, gold, and/or other material that can sense a voltage such as a neural voltage. When a signal, such as neural signal 150A, is sensed at the input stage, the electrode 104A and/or penetrating probe 105A carry this signal to a transconductance device 202. In the example of FIG. 2A, the transconductance device is implemented as a CMOS Field Effect Transistor (FET), although other types of transistors, such as a thin-film transistor (TFT), bipolar junction transistors (BJT), and/or a transistor implemented on flexible substrates may be used as well. In the example of FIG. 2A, the electrode 104A is coupled to the gate 207A of the FET 202, which has its source (or, e.g., an emitter) terminal 207B coupled to a power source 205 (which in this example is 0.8 volts although other voltage values may be used) and the FET's drain (or, e.g., collector) terminal 207C provides an output for the transconductance device 202.

The transconductance device's 202 drain terminal 207C is coupled to an input 208 of a three-stage ring oscillator 210, although the ring oscillator may implement with more stages. The ring oscillator oscillates at a specific frequency, when there is an input voltage present. For example, when the neural signal is detected and received via the electrode 104A and the penetrating probe 105A, this small voltage (which in this example is 1 millivolt) is detected (e.g., sensed) by the transconductance device 202 and is provided at the output 207C, which is further coupled to the input 208 of the oscillator 210. The oscillator 210 may then output 215 a signal (e.g., an oscillator output signal) based on the amount of voltage present at the input 208. In other words, the oscillator may output 215 a signal at a given frequency (or modulated at given frequency) based on the voltage value at the input 208. In this example, the oscillator 210 serves as a voltage controlled oscillator or a voltage to frequency converter. At FIG. 2A, the output 215 of the oscillator 210 serves as an input to an amplifier 212. The amplifier 212 amplifies (e.g., maximizes) the voltage swing of the modulated signal, and the amplifier 212 couples the signal onto the bus 130 through the coupling capacitor 108A.

Although FIG. 2A depicts a ring oscillator, the oscillatrode circuit may be implemented in other configuration such that a voltage sensed by an electrode is frequency modulated and coupled to a common bus.

Figure 2B:
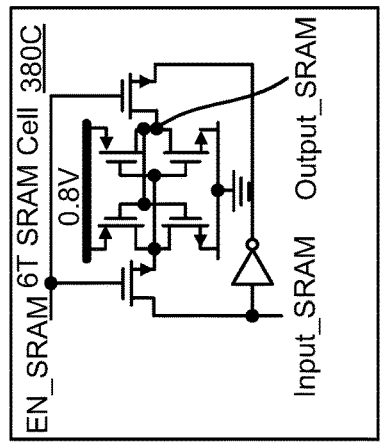
FIG. 2B depicts examples of circuits, in accordance with some example embodiments.

FIG. 2B depicts additional circuits, in accordance with some example embodiments. Circuit 380A depicts another example of an oscillatrode circuit. Unlike the oscillatrode circuit of FIG. 2A, the oscillatrode circuit at 380A includes (1) two unit elements 266A-B of transconductance device 202 controlled by SW1 and SW2; (2) a 2:1 chopper-stabilizing switch 263 between the electrode 104A and the gates of the transconductance device 202 to alternate the voltage bias between the electrode 104A (e.g., sensing signals from the brain tissue) and a reference voltage 266C provided by the electronics; and (3) two enabling control bits, EN1 and EN2, provide independent control of the oscillator and the buffer circuits 366X and 366Y. Circuit 380B depicts the architecture of a 4-bit shift-register and a 4-bit local SRAM implemented within one oscillatrode circuit. The EN1, EN2, SW1 and SW2 outputs of circuit 380B are provided as control signals to circuit 380A as shown. Circuit 380C depicts an example implementation of a 6-T SRAM cell shown at circuit 380B.

Referring again to FIG. 1A, the system 100 may require little or no pre-conditioning circuit, such as analog signal amplification, low-pass filtering, and/or digitization, as the neural signals 150A-N may each be directly transformed to a frequency-modulated carrier as shown at FIG. 2A, for example. Moreover, the carrier frequencies from each carrier may not be pre-defined but rather randomness in frequency may be utilized to create frequency spacing between carriers, although other techniques may be used to mitigate overlap.

In some embodiments, the oscillatrode circuits 102A-N may each be designed to operate at non-overlapping frequencies to ensure orthogonality between each channel. This can be achieved by (1) having different transistor aspect ratios (width and length, W/L) in the transconductance device 202 of each oscillatrode (2) having a different quantity of inverter stages in each ring oscillator (e.g., 3 stages, 5 stages, 7 stages, 9 stages, 11 stages, and so forth); (3) having different sized inverter stages within each ring oscillator (e.g., the physical size of each inverter may be varied); (4) having different capacitive loading (e.g., through addition of extra parasitic metal routing) at the output of each inverter within a single ring oscillator; and/or (5) having a combination of one or more of (1)-(4).

To ensure orthogonality between each frequency channel (e.g., the frequency tones output by each oscillatrode circuit), the center frequencies of each oscillator in the oscillatrode circuits 102A-N should not overlap. Although systematic frequency gradient may be introduced by design, as mentioned in the previous paragraph, random electrode offsets ranging from about 5 millivolts (mV) to about 50 mV and mismatches in the devices and metal routing may provide natural frequency differences between the center frequencies of the oscillatrode circuits 102A-N. However, a calibration process may still be used to reduce significant frequency overlap between the oscillatrode circuits 102A-N.

The center frequency calibration process may be performed by sequentially turning on each oscillator at a given oscillatrode circuit 102A-N, recording the respective oscillation frequency, and performing frequency adjustment when frequency overlapping is observed. Both the "enable" sequence and frequency adjustment is provided by on-chip shift registers using digital bits. The frequency adjustment is controlled by (1) enabling (e.g., turning "on") different quantities of capacitive-loading elements (e.g., adding or removing capacitors, at the outputs of the inverter in each ring oscillator) and/or by (2) changing the current supplied to the oscillators by adjusting the transistor aspect ratios (e.g., width and length, W/L) digitally (see, e.g., FIG. 2B at 380A) or the biasing of the transconductance device 202. The control bits may be stored in a local memory, such as SRAM cell (see, e.g., 380C at FIG. 2B). During the calibration, each electrode oscillator is enabled sequentially within a time window. The single-wire bus output may be sampled at a high-speed followed by Fast Fourier Transform (FFT) to quantize the oscillation frequency, or may be monitored through spectrum analyzer employing frequency sweeping. If two electrode oscillators are found to have overlapping oscillation frequencies, one of the SRAM cells in an oscillator may be programmed to adjust its oscillation frequency. The entire calibration procedure may be repeated multiple times to ensure non-overlap in the oscillation frequencies between the oscillatrode circuits.

At FIG. 2A, the EN 218 may provide the enabling "on" signal for each oscillator through a NAND or a NOR gate. In the NAND case, the oscillator will remain "OFF" when the EN 218 is tied to low voltage signal. This enabling/disabling scheme offers system flexibility to disable a given electrode (e.g., if the electrode is defective).

Figure 3A:
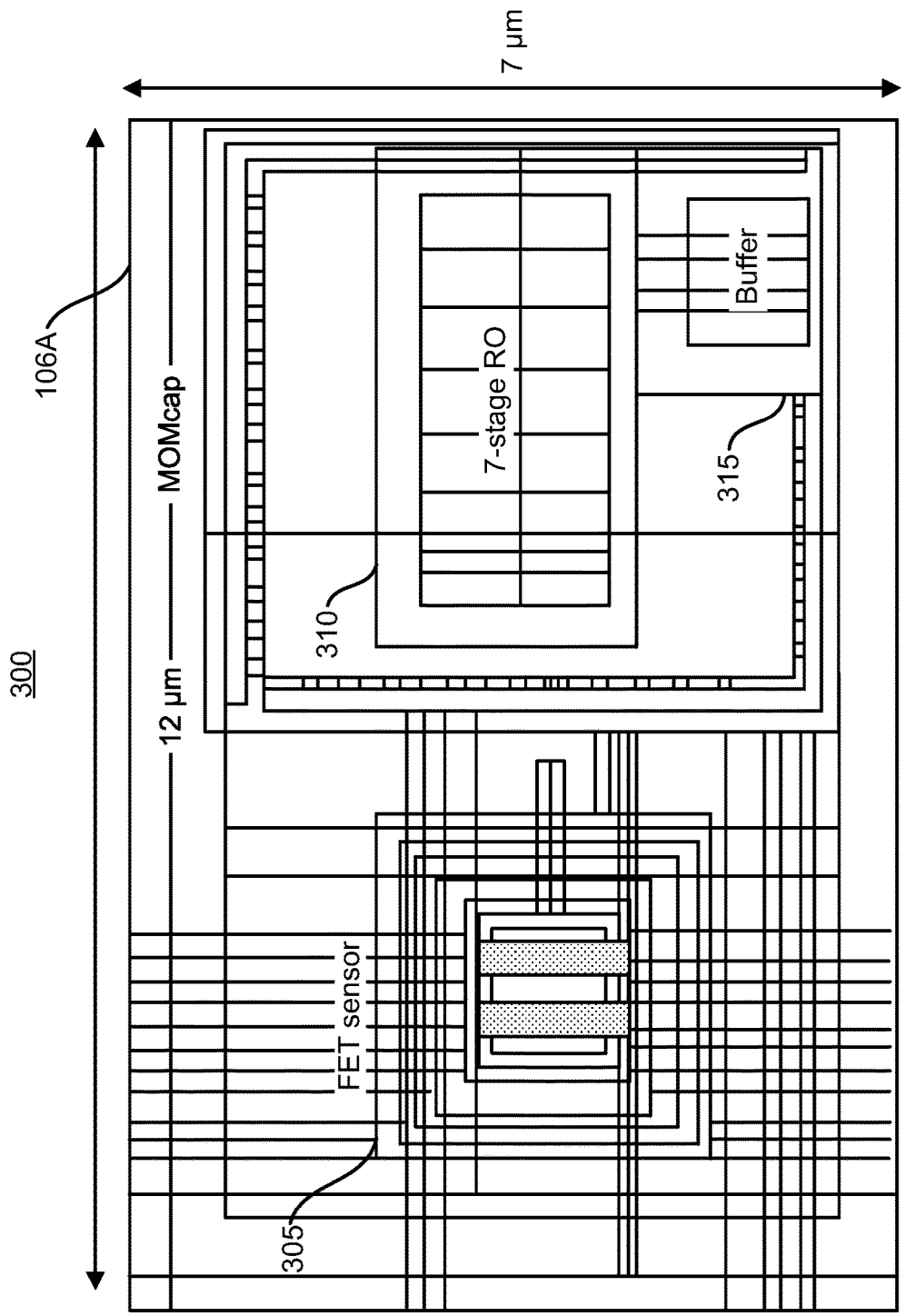
FIG. 3A depicts a picture of circuitry including an oscillatrode, in accordance with some example embodiments.

FIG. 3A depicts a picture 300 of circuitry including an oscillatrode such as oscillatrode 106A. In the example of FIG. 3A, the circuitry has dimensions of 12 microns and 7 microns, although other sizes may be implemented as well. The circuitry includes a portion 305 in which the electrode 104A and switch 202 are implemented, and another portion in which the oscillator 310 is implemented. In the example of FIG. 3A, the oscillator is implemented as a 7-stage ring oscillator, although the oscillator may be implemented in other forms. The circuit also includes a buffer 315 for signal amplification and isolation, similar to 212 in FIG. 2A. The coupling capacitor 108A may be implemented with, for example, a metal-oxide-metal capacitance from the metal stacks from the VLSI fabrication, although other types of capacitors may be implemented as well.

Figure 3B:
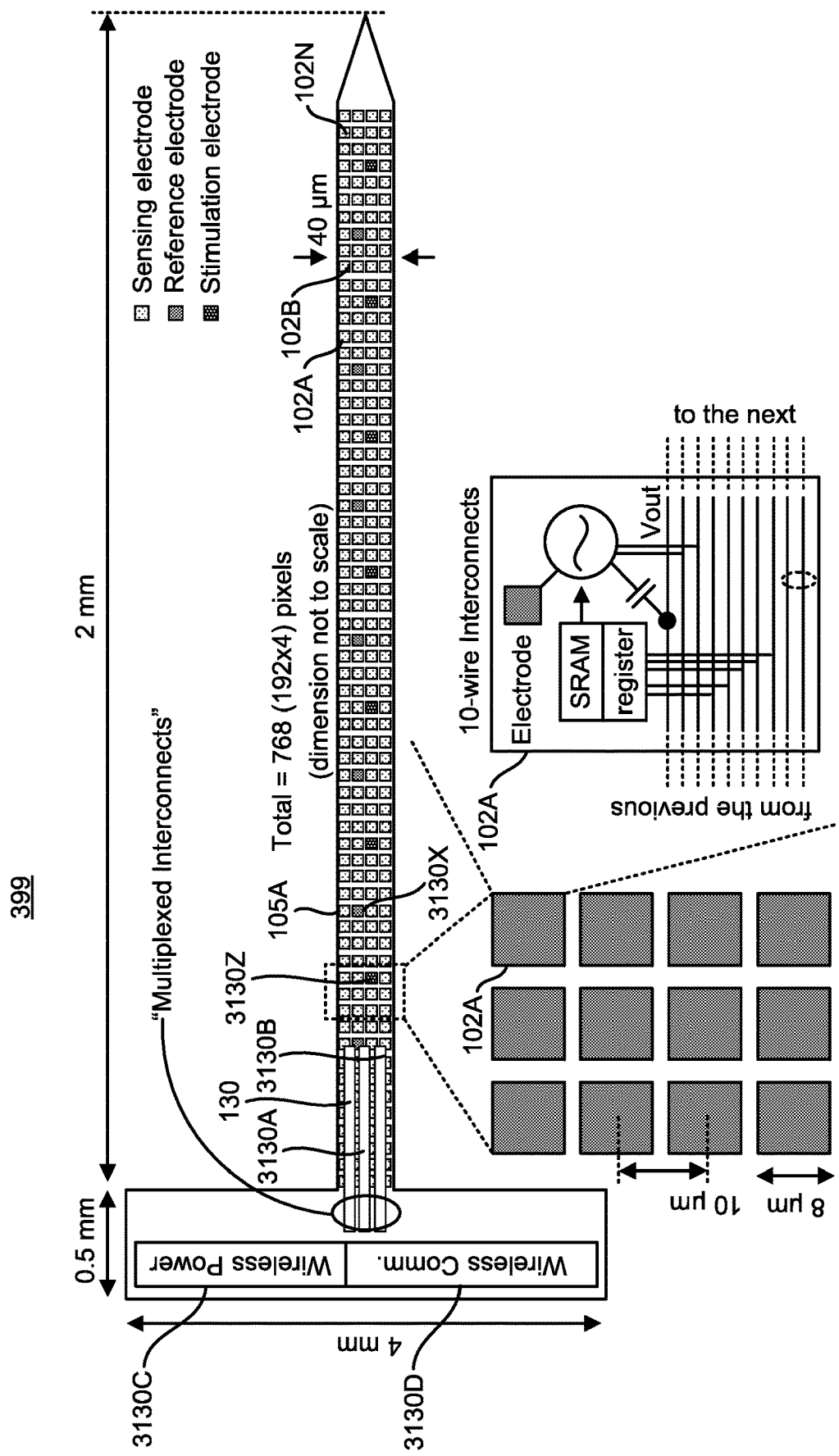
FIG. 3B depicts an example of a probe, such as a neural probe, in accordance with some example embodiments.

FIG. 3B depicts an example of a neural probe 399 including a penetrating probe 105A. The oscillatrode circuitry (represented by squares) 102A-N may include in the neural probe and, in particular, on the penetrating probe 105A. In this way, the plurality of oscillatrode circuits may sense the tissue and directly couple corresponding frequency tones (which are frequency division multiplexed) to the shared bus 130.

In the example of FIG. 3B, the penetrating probe 105A is 2 millimeters by 40 micrometers, although other dimensions may be used as well. In the example of FIG. 3B, the plurality of oscillatrode circuits may couple to a shared bus 130. The oscillatrode circuits 102A-N and so forth may share interconnects 3130A and 3130B, which may provide power and/or control. The example of FIG. 3B also depicts wireless communication circuitry 3130D which may include a wireless transceiver (see, e.g., FIG. 4 at 405) and wireless power circuitry 3130C which may provide a wireless power source that can be charged inductively, for example. In the example of FIG. 3B, there may also be provided a reference electrode 3130X measuring the averaged potential in the brain tissue and stimulation electrodes 3130Z to active the nearby neurons.

Figure 3C:
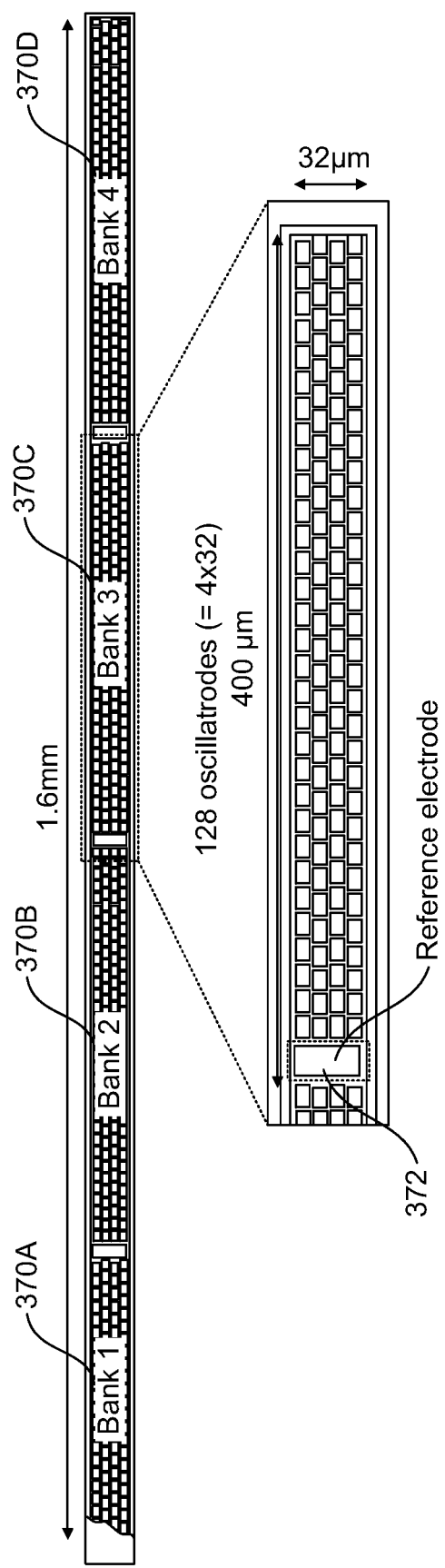
FIG. 3C depicts a picture of circuitry including an oscillatrode, in accordance with some example embodiments.

FIG. 3C shows an example of a photo of a neural probe device with 512 oscillatrode circuits. These circuits are divided into four banks 370A-D, with each bank consisting of 128 oscillatrode circuits. The neural probe has a total length of 1.6 millimeters and a width (or diameter) of 40 micrometers. Each bank is coupled to its own common bus 130. For example, the oscillatrode circuits in bank 370A share a first, single wire common bus, the oscillatrode circuits in bank 370B share a second, single wire common bus, and so forth. These common buses traverse the cranium using wired or wireless links as further described below with respect to FIG. 4. In the example of FIG. 3C, each bank includes a single reference oscillatrode to be shared across all oscillatrodes within the bank. For example, reference oscillatrode 372 may provide a reference potential, which measures the averaged potential in the brain tissue, to all of the oscillatrodes within the bank 370C.

Figure 3D:
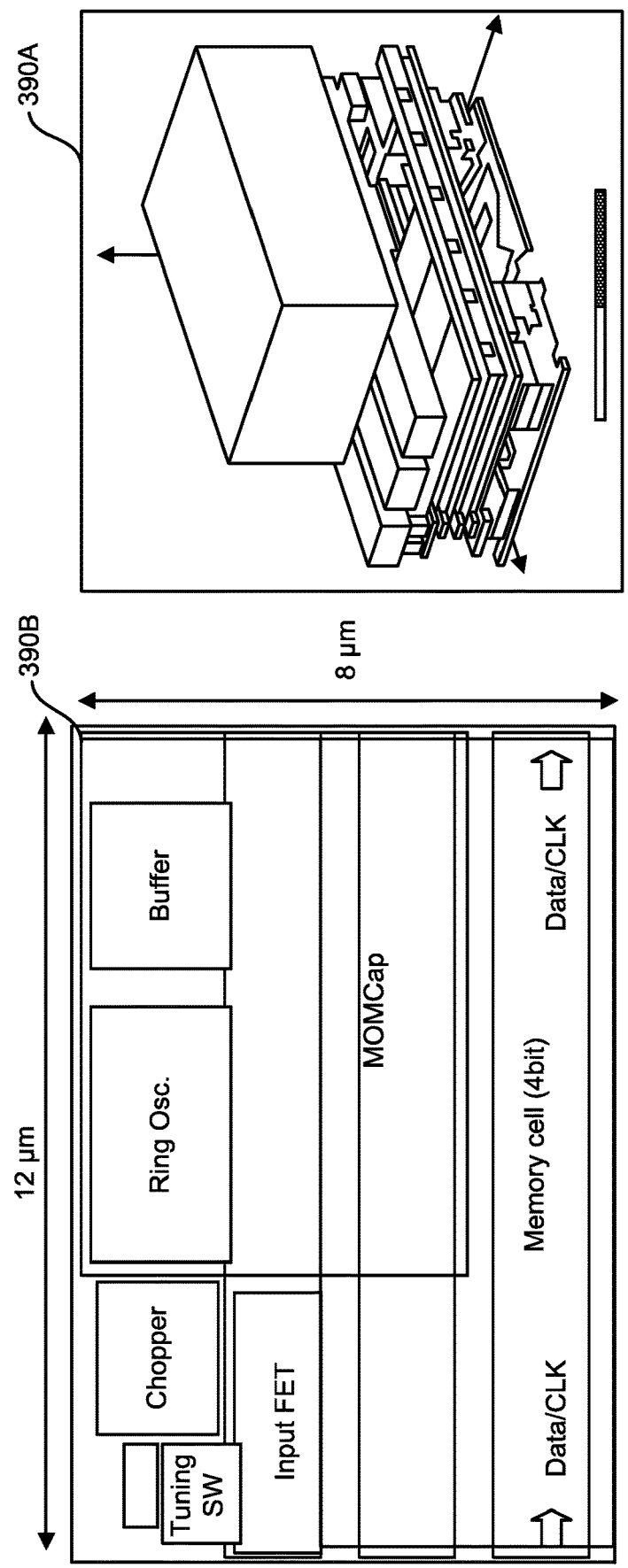
FIG. 3D shows a picture of an oscillatrode circuit and a three-dimensional rendering of the circuit shown, in accordance with some example embodiments.

FIG. 3D shows a picture 390B of an oscillatrode circuit and a three-dimensional rendering 390A of the circuit shown at 390B. In this example, the oscillatrode circuit has dimensions of 12 micrometers by 8 micrometers, and include four D-flip flops which may be configured to provide the D-flip flops shown at circuit 380B. These flip flops may be implemented in static CMOS, although other implementations may be realized as well.

Figure 4:
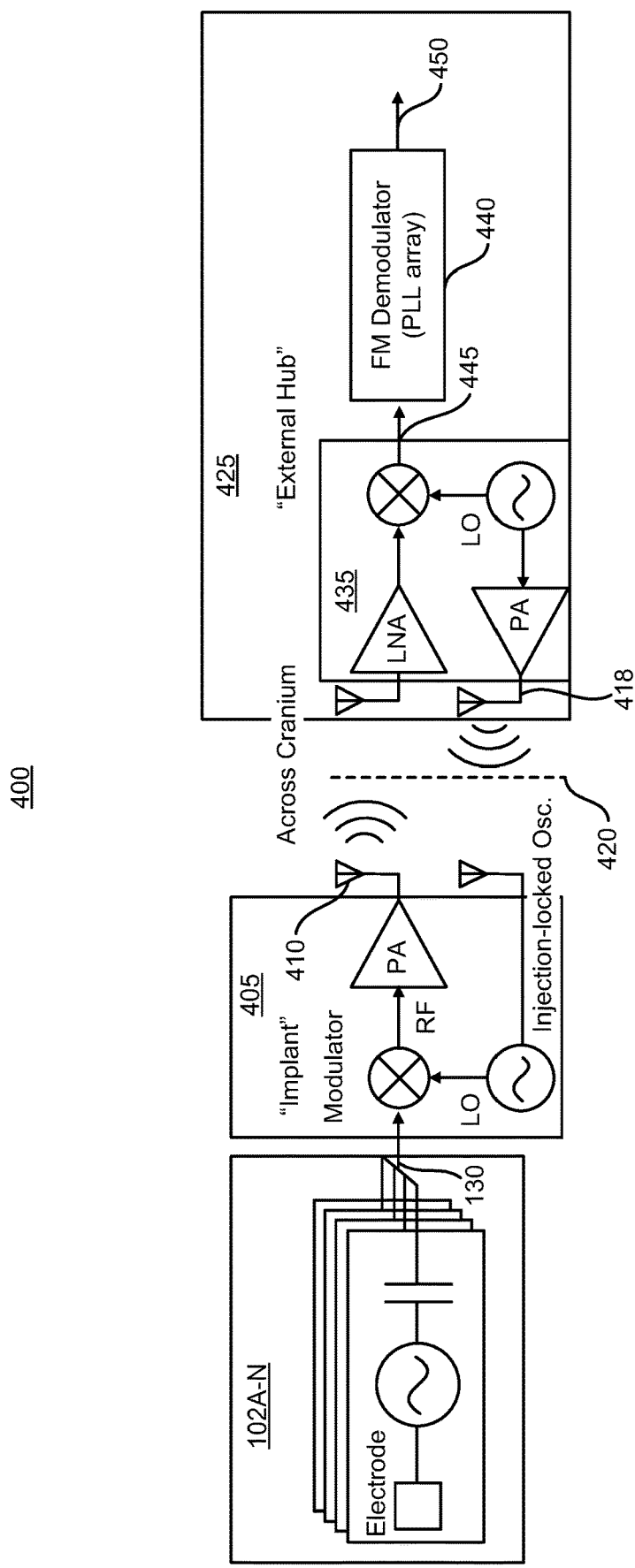
FIG. 4 depicts an example of a system, in accordance with some example embodiments.

FIG. 4 depicts an example of a system 400, in accordance with some example embodiments. The system may include a plurality of oscillatrode circuits 102A-N coupled to a bus 130. As noted, the FDM signal (which is generated by the oscillatrode circuits 102A-N and is carried by the bus 130) may go through the cranium 420 via a wired connection or a wireless link. The example of FIG. 4 depicts the wireless example. As shown, the bus 130 is coupled to a wireless transceiver 405, which is implanted within the cavity of the cranium such that the probe can make contact with the neural tissue being monitored. This wireless transceiver 405 may generate a radio frequency (RF) signal (which carries the information contained in the FDM signal from the plurality of oscillatrode circuits 102A-N) for wireless transmission via antenna 410.

The receiver 425 (labeled "External Hub") may be located external to the cavity of the cranium 420. In the example of FIG. 4, the receiver includes a wireless transceiver 435 to receive from antenna 418 the RF signal (which is transmitted via antenna 410). The wireless transceiver 435 demodulates the RF signal to recover the FDM signal generated by the plurality of oscillatrode circuits 102A-N. The receiver may also include an FM demodulator 440 to demodulate the FDM signals into voltages representative of the voltages 150A-N. In other words, the output at 450 may include a first voltage signal corresponding to the detected neural voltage 150A, a second voltage signal corresponding to the detected neural voltage 150B, and so forth.

Figure 5A:
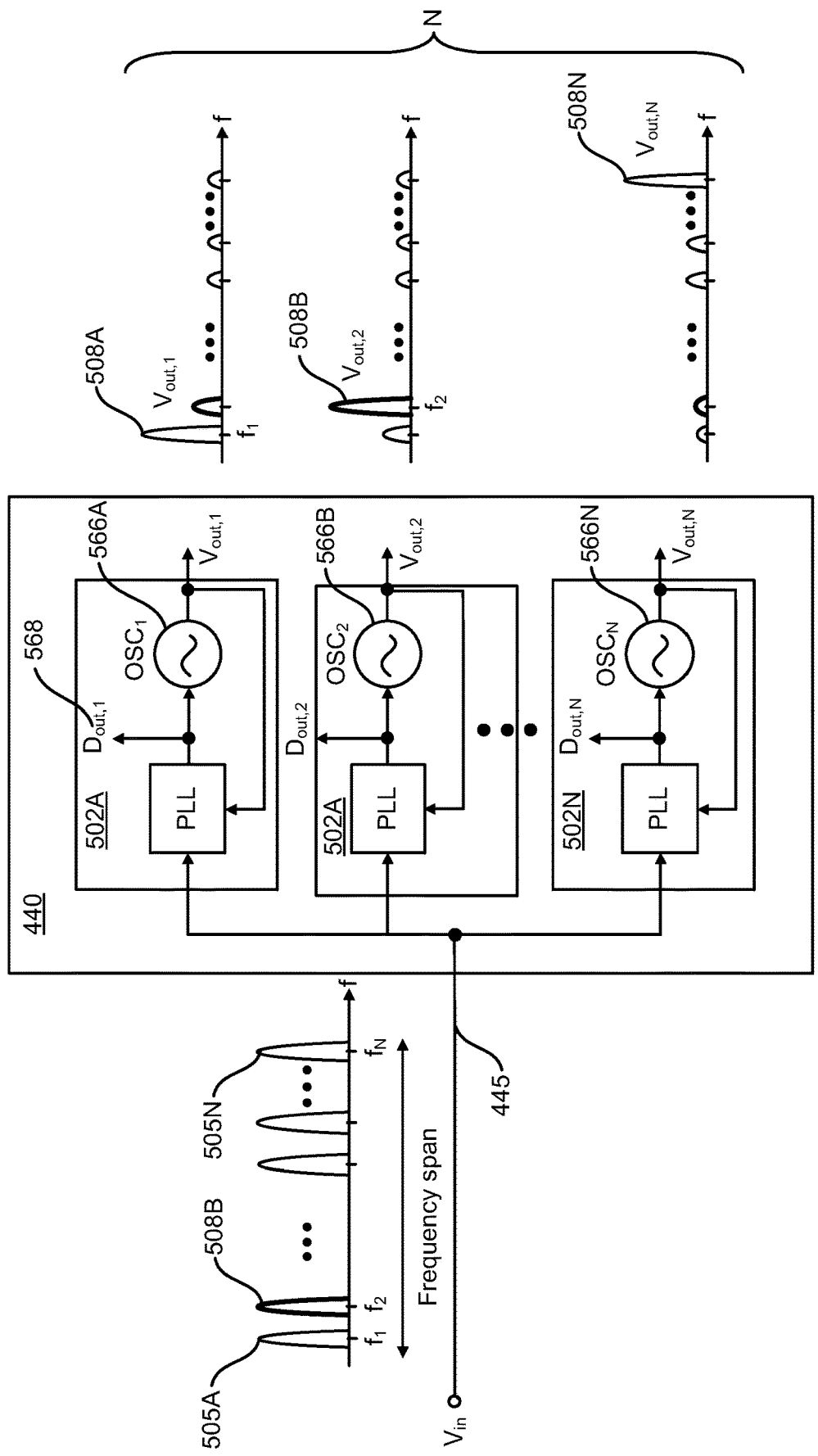
FIG. 5A depicts an example of a demodulator including a phase locked loop, in accordance with some example embodiments.

FIG. 5A depicts an example of the demodulator 440. The demodulator 440 may include one or more phase lock loop circuitry 502A-N to demodulate the input 445 FDM signal. For example, the demodulator's 440 output 508A is at a given voltage value when the tone 505A is present in the FDM signal. Likewise, the phase lock loop circuitry 502B outputs a given voltage value 508B when there is a tone 505B present in the FDM signal, and the phase lock loop circuitry 502N outputs a given voltage value 508N when there is a tone 505N present in the FDM signal. The output 450 (FIG. 4) includes the voltages detected and output at 508A-N. These outputs thus represent the neural voltages 150A-N detected by the neural probe (see, e.g., FIG. 1A).

Each PLL 502A-N may perform frequency tracking against each individual oscillatrode, and the frequency-modulated information is reflected at the output of the PLL loop filter, which can be further digitized for downstream signal processing.

The array of phase-locked loops 502A-N performs a FM demodulation on each of the FM carriers 505A-N to recover the signals 508A-N. The phase-locked loops may be implemented with sampling-based phase detection and digital loop filter to provide additional spectral filtering and digitization functionality. To avoid false locking, a voltage-controlled oscillator (labeled "OSC$_1$" 566A, "OSC$_2$" 566B, and "OSC$_N$" 566N) in each PLL may also be frequency pre-calibrated to each tone frequency, such as 505A, 505N, etc. The PLL's loop bandwidth may be selected according to the signal bandwidth, which in may be about 10 kHz in neural recording applications. A sampler-based notch-filter may also be included along with a sampling-based phase detector to reduce channel crosstalk.

In operation, the oscillation frequency of the ring oscillator (RO) in each individual PLL at 502A-N is calibrated using the frequency-calibration loop to minimize the frequency difference against the desired spectral tone from the oscillatrode. This is ensured by the PLL operation that it will lock to the closed spectral tone without false locking. Such a frequency adjustment can be accomplished digitally using either capacitor banks or programmable current digital-to-analog converter (DAC). Once complete, the loop is closed to enable frequency and phase locking to the desired spectral tone from a designated pixel (e.g., electrode) through an adjustment of a loop filter control voltage. The oscillators 566A-N may be implemented as ring oscillators, such as the ring oscillators described with respect to FIG. 2A, although a different type of oscillator may be used as well. Alternatively, it may be preferential to consume higher power (such as 4 times) than the oscillator at FIG. 2A, such that its noise is at least 6 dB lower without dominating the overall front-end noise performance. Conventional phase-and-frequency detector (PFD) implemented with digital logic gates may not preferred in this case as the input is an analog signal with sum of multiple spectral tone, thus lacking distinct pulse transitions. As such, an analog phase-detector may be preferred for use as 502A, for example, in which case the phase lock loop circuitry 502A-N may be implemented with a mixer-based phase detector shown at FIG. 5B. A property offered by the mixer-based phase detector shown at FIG. 5B is its capability to perform spectral filtering.

Figure 5B:
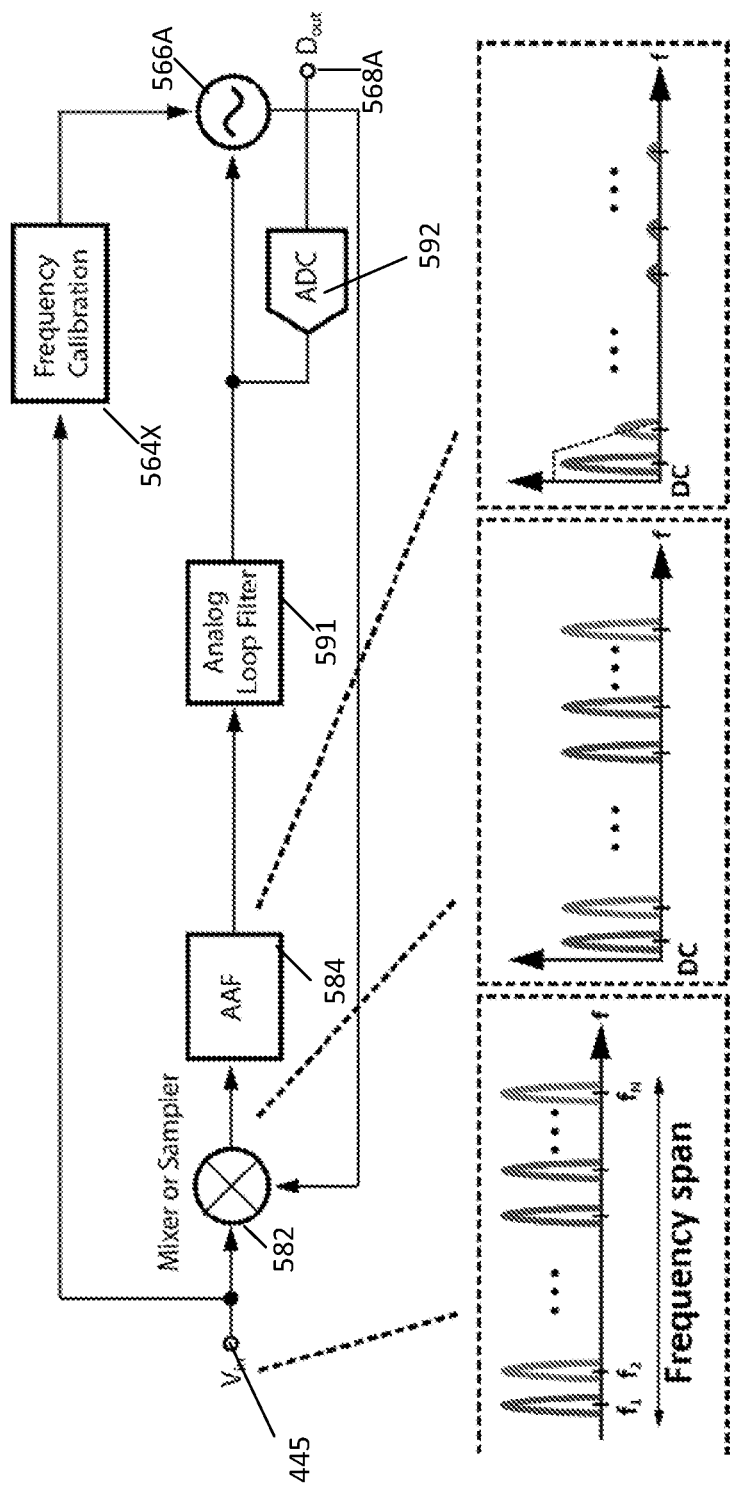
FIGS. 5B-5C depict an example of a phase detector, in accordance with some example embodiments.
Figure 5C:
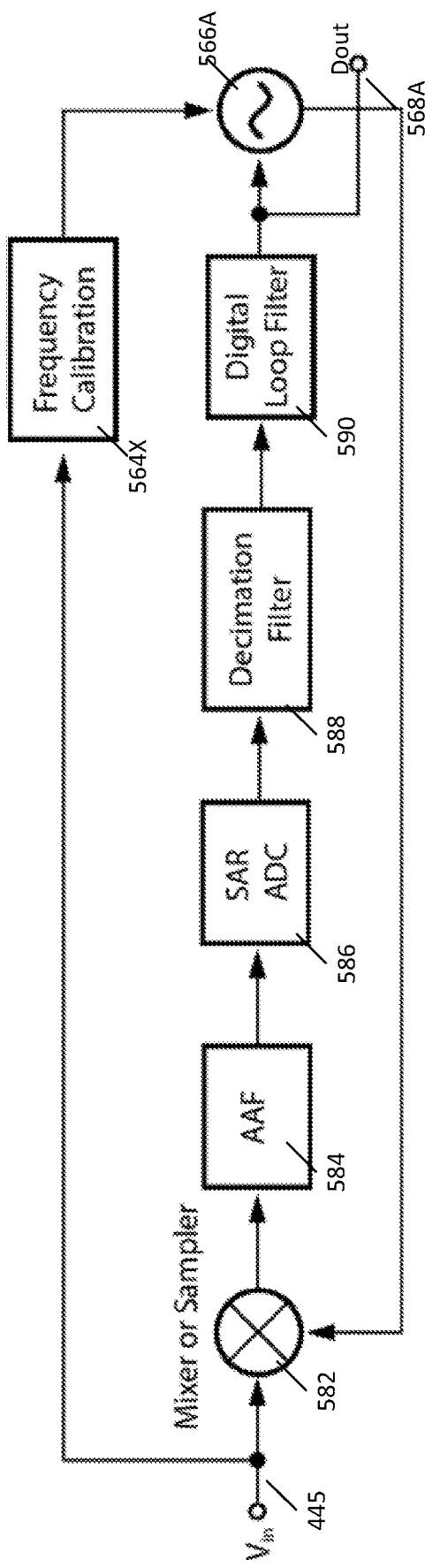

FIG. 5B depicts an example mixer-based phase detector including a mixer 582, coupled to an analog anti-aliasing filter (AAF) 584 coupled to an analog loop filter 591, which is coupled at its output to an ADC 592 (which provides Dout 568A) and an oscillator 568A, The frequency calibration 564X is coupled to Vin 445 and the oscillator 566A. FIG. 5C shows an alternative PLL architecture. In the example of FIG. 5C, the AAF output is provided to a SAR ADC 586, which is further coupled to a decimation filter 588. The decimation filter output is provided to a digital loop filter 590, the output of which is provided to the oscillator 566A and provides Dout 568A. Referring to FIG. 5B, a mixer-based detector 582 performs down conversion of the input spectral-rich signal to near DC. An analog anti-aliasing filter (AAF) 584 is then used to attenuate the out-of-band signals. Such an analog filter can be merged into the analog loop filter 591 of the PLL. In this case, an additional analog-to-digital converter (ADC) 592 is required to provide digitization from the control voltage of the PLL. A mixer-based phase detector can be implemented with current-mode-logic; as an alternative, a sampler is employed. In the later, care must be taken to prevent high-frequency tones from aliasing into band-of-interest. Note that the ADC 592 can be placed right after the spectral-filtering loop filter whereas the digitized signal is fed into a digital loop filter that provides a sharper roll-off while occupying a smaller silicon area. The digital loop filter 590 may be implemented with scaling elements and accumulators. The output of the digital loop filter 590 serves as the demodulated and digitized signal output 568A. The ADC can be implemented with successive-approximation ADC (SAR-ADC 586) or a voltage controlled oscillator (VCO)-based ADC for low power and small area.

In short, the PLL array of FIG. 5A involves two-step operation. In the first step, each oscillatrode in the neural probe is enabled one at a time. During this time, frequency calibration 564X on the RO in each PLL at the receiver is performed. The results are stored in the registers of the frequency-calibration loop in each PLL. In the second step, each oscillatrode is enabled sequentially, and the corresponding PLL at the receiver performs phase acquisition and loop locking. In other words, only the oscillatrode 1 and PLL 1 are enabled in the beginning. Only after PLL 1 locks to the phase and frequency of the oscillatrode 1 will oscillatrode 2 and PLL 2 be enabled. After the locking of PLL 2, oscillatrode 3 and PLL 3 are enabled for operation. This process may be repeated until all the desired oscillatrodes are enabled and the corresponding PLL performs successful settling. The digitized data output 568 will be streamed out to another device for further data processing.

Figure 6:
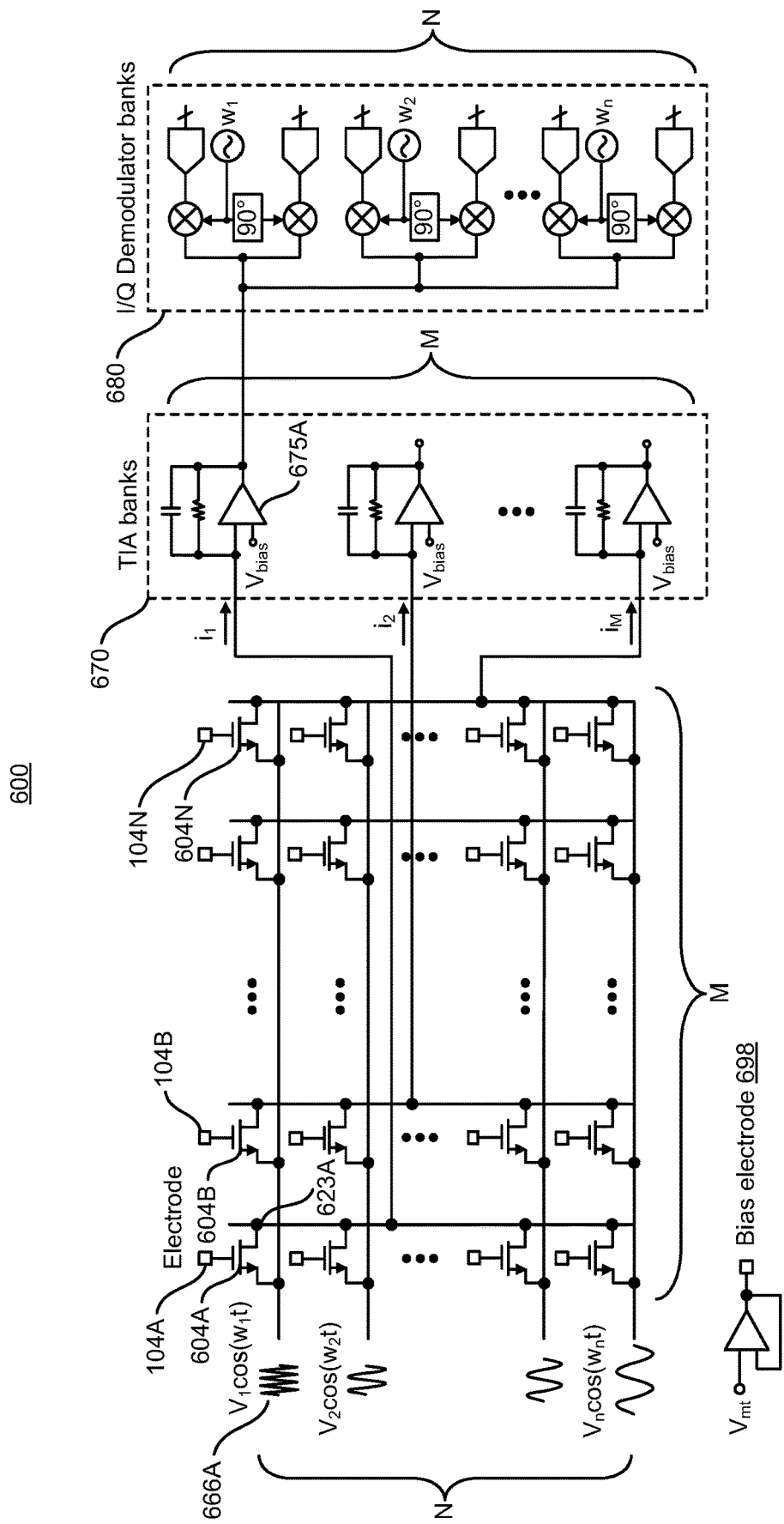
FIG. 6 depicts an example of a mesh configuration for frequency division multiplexing sensed signals, in accordance with some example embodiments.

FIG. 6 demonstrates an example of a mesh 600 for multiplexed detection over large number of sensing elements. Here, field-effect transistors (FETs) 604A-N are used as signal transducers. The gates of the FETs are connected to the electrodes 104A that interfaces the tissue, such as the neural tissue. The bias electrode 698 may introduce a bias voltage into the tissue being sensed. This enables the FETs to sense the change in neural voltage relative to the voltage of the bias electrode. This bias electrode may be used in some of the embodiments disclosed herein. The presence of the action potential from neurons (e.g., the neural signals 150A-N) will impinge onto a gate of the FET and modulate the FET channel resistance. The channel resistance can be measured through current with source-drain biasing. Here, the resistance is quantified through AC impedance measurements. In impedance measurements, a small-amplitude sinusoidal signal, such as 666A, is injected on one side of the transistor (e.g., the drain of the FET 604A) while the other side (the source) 623A is connected to the input of a transimpedance amplifier 675 (TIA), as shown in FIG. 6. The input of the transimpedance amplifier 675A serves as a virtual ground, so the resultant current is the ratio of the voltage amplitude and the FET's 604A channel resistance.

To enable large-scale detection across a 2D array, the FETs at FIG. 6 are in a N by M 2-D mesh network. In each row (column), N number of FETs are connected through their drains (or sources). Each row line is driven with a sinusoidal excitation voltages 666A-N with an amplitude Vi at frequency ωi. The multiplexing for simultaneous measurement is achieved by having distinct and orthogonal operating frequencies on each row line. The current that flows into the first column TIA 670 through the shared column line is:

$$i_1(t) = \frac{V_1\cos(\omega_1 t)}{Z_{1,1}} + \frac{V_2\cos(\omega_2 t)}{Z_{2,1}} + \ldots \frac{V_n\cos(\omega_n t)}{Z_{n,1}} = \sum_1^n \frac{V_i\cos(\omega_i t)}{Z_{i,1}},$$

where $Z_{i,1}$ is the impedance of the $i^{th}$ FET in the first column. After TIA amplification at 670, the information of each FET resistant is separated and demodulated with I/Q down-converting mixers and ADC. By the same token, the current that flows into the second column TIA through the shared column line is:

$$i_2(t) = \frac{V_1\cos(\omega_1 t)}{Z_{1,2}} + \frac{V_2\cos(\omega_2 t)}{Z_{2,2}} + \ldots \frac{V_n\cos(\omega_n t)}{Z_{n,2}} = \sum_1^n \frac{V_i\cos(\omega_i t)}{Z_{i,2}}.$$

the current that flows into the $M^{th}$ column TIA 670 through the shared column line is:

$$i_M(t) = \frac{V_1\cos(\omega_1 t)}{Z_{1,M}} + \frac{V_2\cos(\omega_2 t)}{Z_{2,M}} + \ldots \frac{V_n\cos(\omega_n t)}{Z_{n,M}} = \sum_1^n \frac{V_i\cos(\omega_i t)}{Z_{i,M}}.$$

Like FIG. 1A, the mesh at FIG. 6 also provides frequency-division multiplexing. As such, in a general sense, the mesh 600 may be considered a variant of the oscillatrode depicted at FIG. 2A and 380A at 2B. A difference (when compared to FIG. 1, for example) is the frequency of the operation is more well-defined and is generated on-chip with high accuracy crystal oscillators. This makes the I/Q demodulating 680 implementations simpler, without sequential enabling and locking of the PLL, as shown at FIGS. 5A-C, for example.

Figure 7:
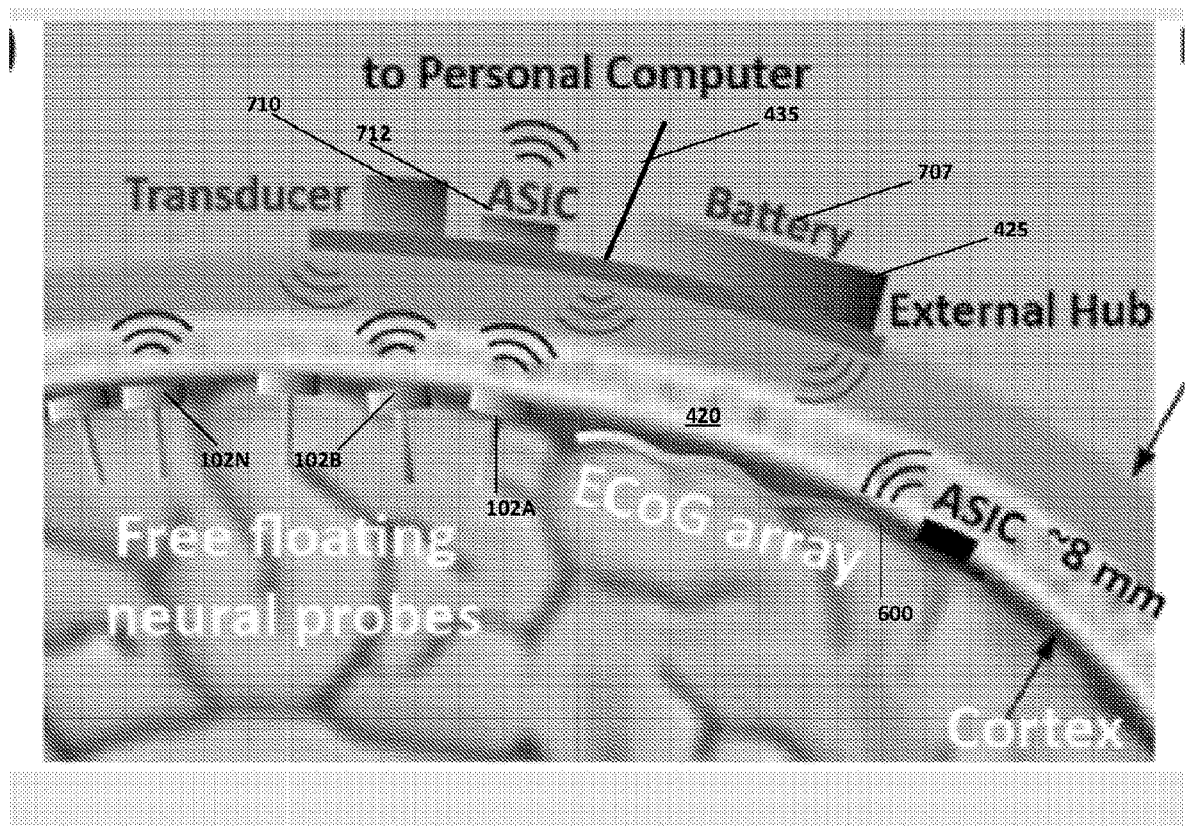
FIG. 7 depicts the neural probe and mesh implanted within the cranium, in accordance with some example embodiments.

FIG. 7 depicts a cranium 420 including oscillatrode circuits 102A-N implanted within the cranium to enable measurements of neurons in the neural tissue. The oscillatrodes 102A-N wirelessly transmit (as noted with respect to FIG. 4, for example) the FDM signal from the common bus 130 to a receiver 425 (labeled external hub). This receiver 425 may be coupled (via a wired or wireless link) to other devices, such as a computer, measurement equipment, and/ or the like for processing the neural measurements. The matrix 600 may also wirelessly transmit (as noted with respect to FIG. 6, for example) the FDM signal to the receiver 425 (labeled external hub). In the example of FIG. 7, the receiver 425 may include a power source, such as battery 707 or other type of power source, a transducer 710 such as RF antennas to transmit power and to receive data. In the example of FIG. 7, the demodulated output of the FM demodulator (see, e.g., FIG. 450) may be carried to other devices via a wired 435 or wireless 712 link.

Figure 8A:
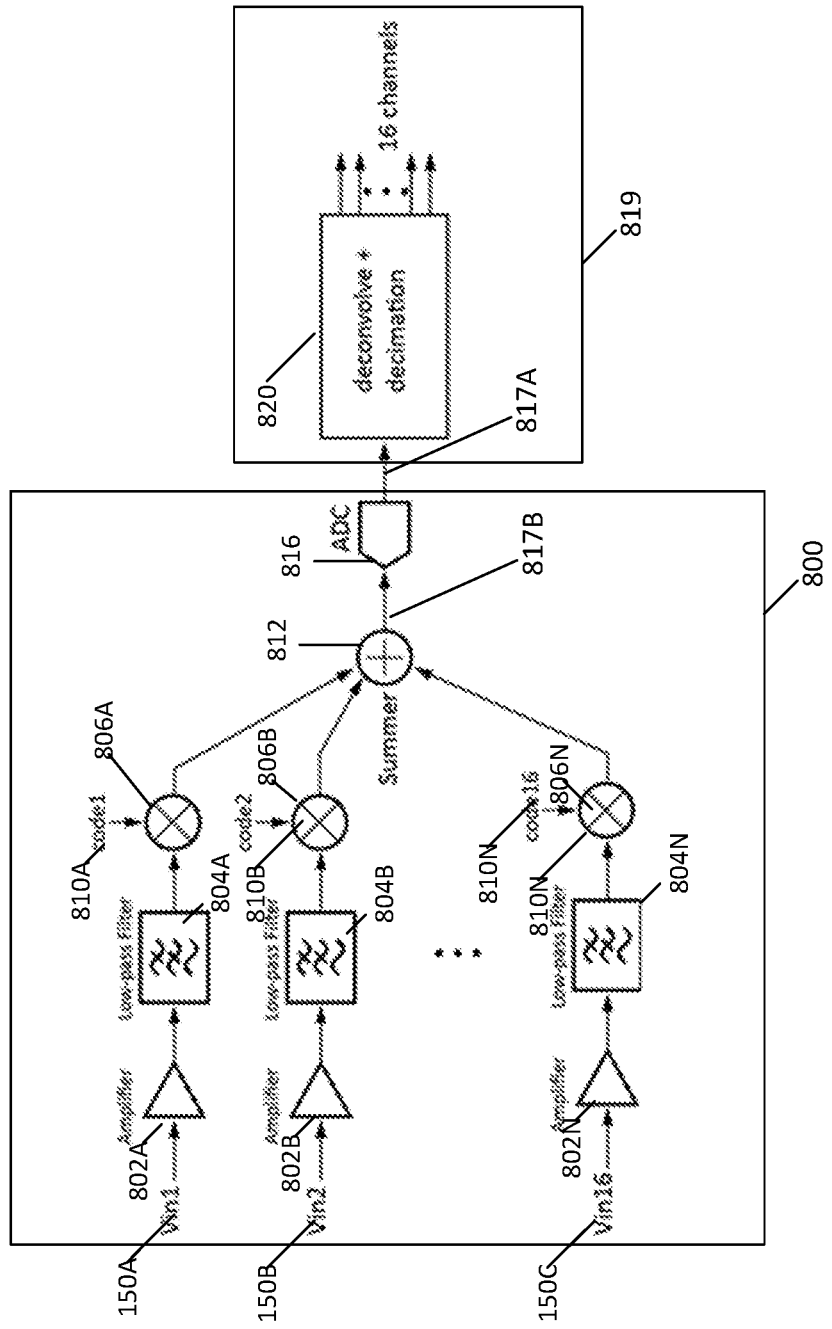
FIGS. 8A-8B depict examples of the use of Walsh codes, in accordance with some example embodiments.

FIG. 8A presents another multiplexing technique for simultaneous recording from a range of recording elements based on Walsh coding. FIG. 8A includes a probe 800, such as a neural probe. The probe may include electrodes to sense incoming signals, such as neural signals 150A-N, which may be amplified 802A-N, low pass filtered 804A-N, and then multiplied 806A-N by Walsh codes 810A-N, and the output of the multipliers 806A-N is summed 812 and then digitized 816 (e.g., using a single voltage-mode analog-to-digital). This digitized signal may be transmitted via a wired or wireless link 817A through the cranium to a receiver 819. In some implementations, the ADC 815 is external to the cranium, in which case the wired or wireless link 817B carries the summer 812 output signal through the cranium to a receiver including ADC 816. The receiver may deconvolve the received signal digitally at 820 with the corresponding Walsh codes (which are the same codes as used at 810A-N) to extract individual neural signals 150A-N. However, an issue with employing Walsh coding is in dynamic range requirement for the ADC 815, which needs to be increased with the number of multiplexing elements N, where N being the number of sensing channels that are simultaneously recorded. For example, a dynamic range of 14 bits is required for 16 channels, each having 10-bit requirement.

Figure 8B:
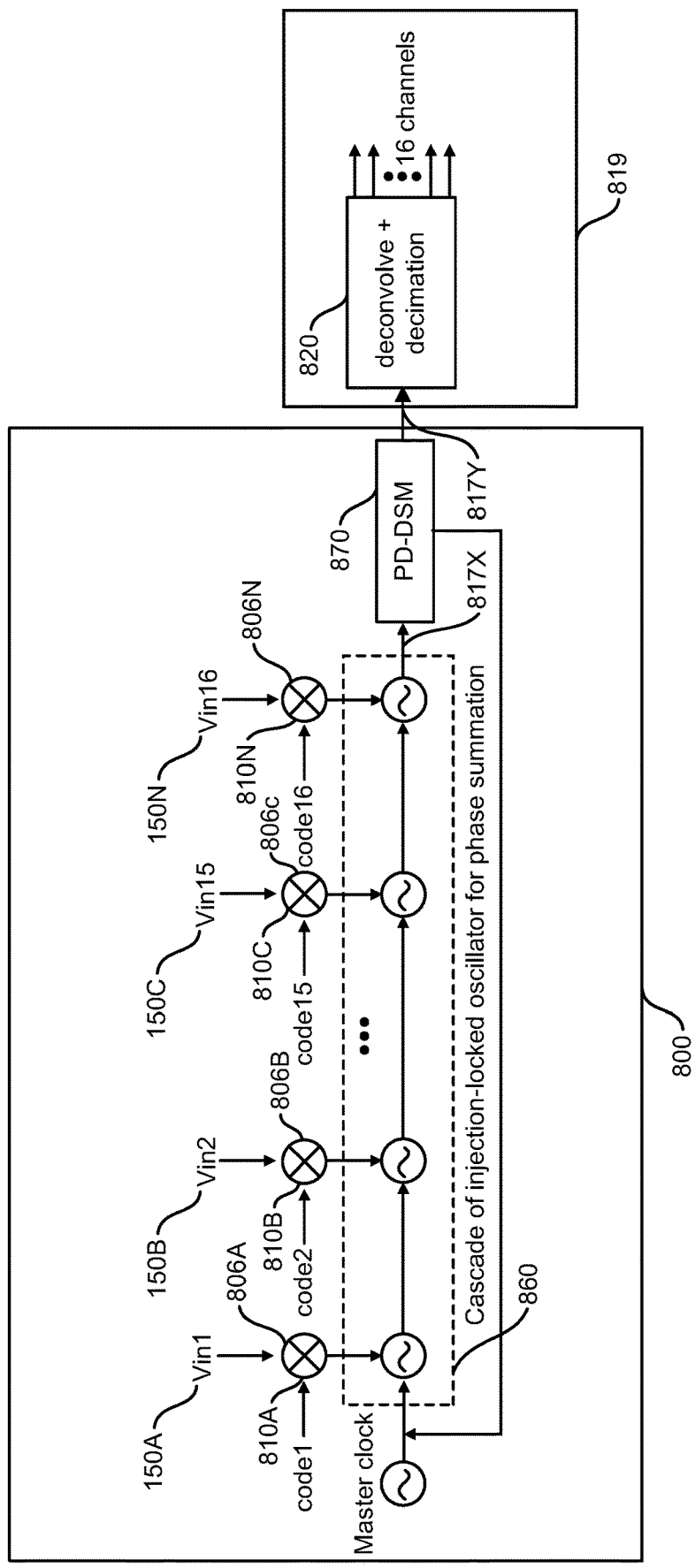

To address this issue, the aforementioned limitation, FIG. 8B configures an array of oscillatrodes to perform Walsh-coding-based multiplexing using phase-domain processing instead of frequency-modulation. First, the sensor signals 150A-N may be again multiplied 806A-N with Walsh codes 810A-N before summation 860. At 860, the summation is performed in the phase domain. This may be accomplished by a cascade of an array of injection-locked oscillators (ILOs) whose phase difference between the input and the output are proportional to the frequency mismatch between the master clock and the free-running frequency of the ILOs. The summed phase 817X is fed into a phase-domain delta-sigma modulator 870, followed by de-convolution and decimation 820. This architecture offers at least two advantages. First, the implementation of the phase-domain delta-sigma modulator (PD-DSM) can be highly digital and scaling friendly, leading to ultra-small circuit area and ease of design porting. Second, the dynamic range can be improved with oversampling, multi-order delta-sigma modulation, relaxing the matching requirement. The maximum number of multiplexed recording channels are limited by the phase-noise accumulation through cascading of ILOs.

In the example of FIG. 8B, the output 817X of the phase summation 860 represents a frequency locked signal having phase information for each of the Walsh coded sensed voltages 150A-N. In other words, the sensed voltages 150A-N are each phase modulated as an output at 817X. In the example of FIG. 8B, a wired or wireless link may carry the output through the cranium to a receiver 819 including the PD-DSM 870 and deconvolver 820. Alternatively, the PD-DSM 870 may be within the cranium, in which case wired or wireless link through the cranium may be at 817Y.

FIG. 9 depicts an example process 900, in accordance with some example embodiments. Although the process is described with reference to FIG. 1A, the other sensing circuits disclosed herein at, for example, FIGS. 1B, 2A, 3B, 3C, 4, 6, 7, 8A, and 8B may be used as well.

At 905, a first plurality of signals, such as the neural signals 150A-N, may be received by an array of electrodes, such as the plurality of electrodes 104A-N. As noted, the electrodes may be implanted in the cranium and make contact with neural tissue to sense the neural signals.

At 910, the first plurality of neural signals may each be modulated. For example, the first neural signal 150A may be frequency modulated to form the first output signal 122A. The other neural signals 150B-N may be similarly modulated. The aggregate of the output signals 122A-N may form a FDM signal. Alternatively, or additionally, the modulation may be phase modulation to form a phase modulated signal. Alternatively, or additionally, the modulation may be code-based modulation. In some embodiments, the modulation is performed based on at least an oscillator. Each of the oscillators may be coupled, via a transconductance device, to a corresponding electrode.

At 920, the first output signal may be coupled to a first bus, such as bus 130, to enable the first bus to carry the first output signal through the cranium to for example a receiver. Likewise, the other output signals 122B-N may also be coupled to the bus. In some embodiments, the oscillator may couple directly to the bus. In some embodiments, a coupling capacitor, such as capacitor 108A and the like, may be used to couple to the bus. The bus may couple to the receiver via a wired and/or wireless link(s). A demodulator may receive the first output signal after it traverses the cranium. The demodulator may output detected signals representative of the first plurality of signals sensed by the first array of electrodes.

In some embodiments, a second array of electrodes may receive a second plurality of signals sensed from neural tissue inside the cranium. As noted above at FIG. 3B for example, a first group of oscillatrodes may couple to a first shared bus, a second group of oscillatrodes may couple to a second shared bus, and so forth.

In some embodiments, wireless powering may be implemented. For example, a multi-step power relaying method may be used to power neural implants under the cranium at a maximum energy efficiency across the skull. For example, the energy may be inductively transferred using larger RF coils at a centimeter diameter across the scalp, followed by power delivery using wires across the skulls, and distributed the power to each implant using ultrasounds. An advantage of wireless powering is that the receiving piezoelectric transducer on the implant may be sub-mm$^3$ volume in contrast to centimeter coil used in RF powering, thereby reducing the implant size.

In some embodiments, the electrodes may be implemented using on-chip pad layer and post-processed to replace the default aluminum with platinum, iridium, or gold. Polymer coating with polypyrrole (PPy) and poly(3, 4-ethylenedioxythiophene) (PEDOT) may further enhance the electrode durability.

In some embodiments, noise, such as flicker noise originated by the electrode oscillators, may be mitigated using circuit techniques such as chopper stabilization. This can be accomplished by chopping the neural voltage-mode signal between a sensing and a reference electrode at a frequency higher than the flicker noise corner frequency. As CMOS ring oscillator exhibits 1/f3 corner about hundreds of kHz, about MHz level chopping frequency may be used. An aspect of high-speed chopping frequency is with respect to the demodulation speed from the PLL, which is limited by the loop bandwidth. This is because PLL needs to re-lock at each transition of frequency hopping due to chopping activity. To remedy this, chopper stabilization techniques may be used. For example, two sets of digital loop filter may be incorporated in the PLL design. A 2:1 multiplexer selects one of the outputs from the digital loop filters to control the VCO control voltage. The operation is in synchronous with the chopping frequency. As each digital filter preserves the status of the PLL from the previous chopping cycle, minimum perturbation on the loop settling is expected. A chopped square-wave may be presented at the output of the digital filters and be demodulated digitally in the baseband signal processing unit.

Wireless clocking communication with multiple neural probes and ECoG arrays in a scaled brain area network may require careful frequency band allocation during the wireless transmission. In some embodiments, there system disclosed herein may wirelessly lock the implanted circuitry's LO frequency (which may feed the oscillatrodes, wireless transceivers, and/or other components within the cranium) from the external receiver 425 using an injection-locking mechanism (see, e.g., FIG. 4). This approach may also save power within the implanted components.

In some example embodiments, there is provided a frequency-multiplexed neural probe architecture for electrophysiological recording using CMOS ring oscillators embedded under the electrodes. An array of oscillatrodes, featuring a pixel size of 7×12 μm$^2$, are distributed along the probe shank and the outputs are coupled and transmitted using a single wire to overcome the space limitation. A 65-nm CMOS prototype including eight ring oscillators is implemented, for example.

Although some of the examples refer to neural probes, the systems and methods may also be applied to other application, such as imaging applications including fluorescence and PET imager, MRI imaging with coil array, DNA microarrays, genome sequencing array, ultrasound imaging, and the like.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random-access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus comprising:
    a common bus; and
    a plurality of oscillatrode circuits coupled to the common bus, the plurality of oscillatrode circuits including a first oscillatrode circuit outputting a first frequency tone when a first input voltage from neural tissue inside a cranium is detected by the first oscillatrode circuit and a second oscillatrode circuit outputting a second frequency tone when a second input voltage from neural tissue inside the cranium is detected by the second oscillatrode circuit, wherein the common bus carries the first frequency tone and the second frequency tone at different frequencies in a frequency division multiplex signal.

2. The apparatus of claim 1, wherein the first oscillatrode circuit includes a first electrode coupled to a first transistor, the first transistor further coupled to a first oscillator, wherein when the first input voltage is detected from neural tissue inside the cranium, the first electrode carries the first input voltage to activate the first transistor, the first transistor outputting a first voltage that initiates the first oscillator to output the first frequency tone, and wherein the second oscillatrode circuit includes a second electrode coupled to a second transistor, the second transistor further coupled to a second oscillator, wherein when the second input voltage is detected from neural tissue inside the cranium, the second electrode carries the second input voltage to activate the second transistor, the second transistor outputting a second voltage that initiates the second oscillator to output the second frequency tone.

3. The apparatus of claim 2, wherein the oscillator comprises a ring oscillator, wherein the transistor comprises a field effect transistor.

4. The apparatus of claim 2, wherein the first electrode comprises a neural penetrating probe, and wherein the first input voltage is a neural voltage generated by neural cells.

5. The apparatus of claim 1, wherein the common bus and the plurality of oscillatrode circuits are implanted within a cranial cavity.

6. The apparatus of claim 5, wherein the common bus provides, via a wired link or a wireless link, the frequency division multiplex signal to a receiver external to the cranial cavity.

7. The apparatus of claim 1, wherein the apparatus comprises or is comprised in a neural probe configured to be implanted within a cranial cavity.

8. The apparatus of claim 6, wherein the receiver demodulates the frequency division multiplex signal to detect signals representative of the first input voltage and/or the second input voltage.

9. A method comprising:
    receiving, at a first array of electrodes, a first plurality of signals sensed from neural tissue inside a cranium;
    modulating each of the first plurality of signals to form a first output signal; and
    coupling the first output signal to a first common bus to enable the first common bus to carry the first output signal through the cranium.

10. The method of claim 9, wherein each of the first plurality of signals is modulated in frequency to form the first output signal comprising a frequency division multiplexed signal.

11. The method of claim 10, wherein the first plurality of signals is modulated in frequency by a plurality of oscillators coupled to a plurality of electrodes.

12. The method of claim 9, wherein each of the first plurality of signals is modulated in phase to form the first output signal comprising a phase modulated signal.

13. The method of claim 9, wherein the common bus wirelessly carries the first output signal through the cranium via a wireless link.

14. The method of claim 9, wherein the common bus carries the first output signal through the cranium via a wired link.

15. The method of claim 9, wherein the method is performed on a neural probe.

16. The method of claim 15, wherein the neural probe is inserted on neural tissue within a cavity defined by the cranium.

17. The method of claim 9, further comprising:
    receiving, at a demodulator, the first output signal traversing the cranium; and demodulating the first output signal to detect signals representative of the first plurality of signals sensed by the first array of electrodes.

18. The method of claim 9, further comprising:

receiving, at a second array of electrodes, a second plurality of signals sensed from neural tissue inside the cranium;

modulating each of the second plurality of signals to form a second output signal; and coupling the second output signal to a second common bus to enable the second common bus to carry the second output signal through the cranium towards a demodulator.

\* \* \* \* \*